US006960230B2

(12) United States Patent
Haefliger

(10) Patent No.: US 6,960,230 B2
(45) Date of Patent: Nov. 1, 2005

(54) LENS IMPLANT

(75) Inventor: Eduard Anton Haefliger, Basel (CH)

(73) Assignee: Accommo AG, Binningen (CH)

( * ) Notice: Subject to any disclaimer, the term of this patent is extended or adjusted under 35 U.S.C. 154(b) by 143 days.

(21) Appl. No.: 10/182,065

(22) PCT Filed: Jan. 26, 2001

(86) PCT No.: PCT/IB01/00091

§ 371 (c)(1),
(2), (4) Date: Jul. 24, 2002

(87) PCT Pub. No.: WO01/56508

PCT Pub. Date: Aug. 9, 2001

(65) Prior Publication Data

US 2003/0004569 A1   Jan. 2, 2003

(30) Foreign Application Priority Data

Feb. 3, 2000   (CH)   ................................... 0212/00

(51) Int. Cl.[7] .............................................. A61F 2/16
(52) U.S. Cl. ..................................... 623/6.39; 623/907
(58) Field of Search ................. 623/4.1, 6.11–6.62, 623/905, 907

(56) References Cited

U.S. PATENT DOCUMENTS

| | | | |
|---|---|---|---|
| 4,608,050 A | | 8/1986 | Wright et al. |
| 4,685,922 A | * | 8/1987 | Peyman ...................... 623/6.13 |
| 4,710,194 A | * | 12/1987 | Kelman ........................ 623/6.6 |
| 4,846,172 A | | 7/1989 | Berlin |
| 4,919,151 A | * | 4/1990 | Grubbs et al. ............... 128/898 |
| 5,002,571 A | * | 3/1991 | O'Donnell et al. ......... 623/6.11 |
| 5,201,762 A | * | 4/1993 | Hauber ....................... 623/6.34 |
| 5,224,957 A | * | 7/1993 | Gasser et al. ............... 623/6.61 |
| 5,275,623 A | | 1/1994 | Sarfarazi |
| 5,620,450 A | | 4/1997 | Eagles et al. |
| 5,674,283 A | * | 10/1997 | Stoy ........................... 623/5.11 |
| 5,725,575 A | * | 3/1998 | O'Donnell, Jr. ............ 623/6.56 |
| 6,210,438 B1 | * | 4/2001 | Sheets et al. ............... 623/6.56 |
| 6,299,641 B1 | * | 10/2001 | Woods ........................ 623/6.37 |
| 6,599,317 B1 | * | 7/2003 | Weinschenk, III et al. 623/6.34 |
| 6,645,246 B1 | * | 11/2003 | Weinschenk et al. ....... 623/6.37 |

FOREIGN PATENT DOCUMENTS

EP   0166051   1/1986

(Continued)

OTHER PUBLICATIONS

Haefliger et al., "Accommodation of an Endocapsular Silicone Lens (Phaco-Ersatz) in the Nonhuman Primate", Ophthalmology, May 1987, vol. 94, No. 5, pp. 471-477.

(Continued)

Primary Examiner—Brian E Pellegrino
Assistant Examiner—Cheryl Miller
(74) Attorney, Agent, or Firm—Greer, Burns & Crain, Ltd.

(57) ABSTRACT

A lens implant serves to replace the lens body of an eye and possesses substantially the same size and shape. It is elastic such that the eye gets back its capability for accommodation. The lens implant has two parts with differing refractive indices and/or differing shapes, which allows to adapt the focal length and shape to specific requirements in simple manner. A distal part is prefabricated as pre-made lens part, while a proximal part can preferably be brought into the lens capsule in a flowable state.

20 Claims, 2 Drawing Sheets

FOREIGN PATENT DOCUMENTS

| | | |
|---|---|---|
| EP | 0337390 | 11/1989 |
| EP | 0537643 | 4/1993 |
| FR | 2698264 | 5/1994 |
| WO | WO 89/00029 | 1/1989 |
| WO | WO 93/02639 | 2/1993 |
| WO | WO 97/26842 | 7/1997 |

OTHER PUBLICATIONS

Haefliger et al., "Accommodation of an Endocapsular Silicone Lens (Phaco-Ersatz) in the Aging Rhesus Monkey", Journal of Refractive & Corneal Surgery, Sep./Oct. 1994, vol. 10, pp. 550-555.

* cited by examiner

LENS IMPLANT

CROSS-REFERENCE TO RELATED APPLICATIONS

This application claims the priority of Swiss patent application No. 0212/00, which has been filed on 3 Feb. 2000 and of which the entire enclosure is included herein by reference.

STATEMENT REGARDING FEDERALLY SPONSORED RESEARCH OR DEVELOPMENT

Not Applicable

INCORPORATION BY REFERENCE OF MATERIAL SUBMITTED ON A COMPACT DISC

Not Applicable

REFERENCE TO A "MICROFICHE APPENDIX"

Not Applicable

BACKGROUND OF THE INVENTION

The invention relates to a lens implant and a kit and a method for producing a lens implant.

A lens implant of this kind is known e.g. from U.S. Pat. No. 4,608,050 or WO 89/00029. It consists of a flexible body which replaces the lens body of the eye. Its shape and size correspond substantially to the one of the typical lens body. Due to its flexibility it allows an good accommodation of the eye.

In order to adjust this lens implant to the individual requirements of an eye, a plurality of implant bodies with various different refractive indices must be may available. This necessitates large expenditures. It has been found, furthermore, that the implant bodies meet the requirements regarding stability and simultaneous accommodation properties in a limited manner only.

FR 2.698.264 describes a lens consisting of two partial lenses between which a filler mass is arranged. The part lenses form the outer shape of the lens and replace the lens capsule. Because to this connecting the lens to the ocular accommodation mechanism becomes difficult. Furthermore, the mechanical properties of the lens are quite different from the ones of a natural lens which renders the accommodation more difficult.

In U.S. Pat. No. 5,275,623 a lens implant is disclosed which consists of a bag with two lenses. The bag is filled by a gas or a liquid. Due its symmetry, however, this lens features properties that basically deviate from the ones of a natural lens so that it hardly can be satisfactory in practice.

BRIEF SUMMARY OF THE INVENTION

Thus, there is the object to provide a lens implant and a kit and a method, respectively of the kind mentioned above which avoid these drawbacks.

This object is met by the lens and the kit and the method, described herein.

The lens implant according to the invention consists thus of a first deformable part and a second part, wherein the two parts have different refractive index and/or different elastic deformability. The first part forms the proximal portion and the second part a distal portion of the lens implant.

Accordingly, the implant can be set together of two differing parts which allows to adjust the focal distance and/or the mechanical properties to suit the respective requirements in a simple way. Thus, the first part can e.g. basically define the size and the volume, respectively, of the lens and ensure the accommodation while by choosing the second part the focal distance and/or the distal shape can be set.

The implant has essentially the shape of the lens body to be replaced so that it fits into the lens capsule and fills same properly. To this end the distal surface of the implant should have a stronger curvature than the proximal surface.

The first part consists preferably of a material which is cureable intraoccularly from a flowable to an elastically deformable state so that it can be made to adapt to the shape of the lens body replaced in a simple way.

For a good accommodating capability the first part should be better elastically deformable than the second part, specifically if latter defines the distal surface of the lens implant.

The second part can be designed elastically deformable, suitable for introduction into the lens capsule in a rolled up or folded state. This is specifically advantageous in combination with a cureable first part, because the first part can be used in this case for filling the lens capsule and guarantees accommodation capability, while the focal distance of the lens implant is given by the second part.

Preferably, the second part forms the distal portion of the lens implant so that it forms a wall which separates the first part from the distal part of the lens capsule. This allows to remove, if necessary, the distal part of the lens capsule if such should become opaque.

The kit for the production of such lenses includes preferably at least one flowable filling material and a plurality of pre-shaped lens parts for the forming the second part. The lens parts feature various different shapes and/or refractive indices. Thus, it is possible to produce with only one single filling material a plurality of lens implants of various differing focal distances and shapes.

BRIEF DESCRIPTION OF THE SEVERAL VIEWS OF THE DRAWINGS

Further embodiments, advantages and applications of the invention follow from the following description with reference to the following drawings.

DETAILED DESCRIPTION OF THE INVENTION

Figure 1:
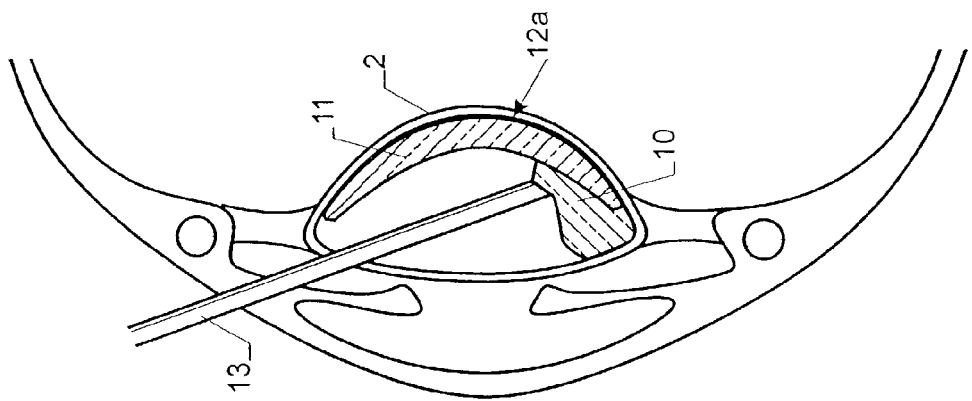
FIG. 1 is a section through a normal eye.

The parts of the eye that are the most important ones in the present context are illustrated in FIG. 1 and include a lens 1, consisting of a lens capsule 2 and a lens body 3, an iris 4 and a cornea 5.

The lens 1 is an elastic body of which the curvature changes upon a contraction of Müller's muscle 6, so that an accommodation of the eye to various focal distances becomes possible. With increasing age, however, the lens body 3 becomes harder, which leads to a partial or complete loss of the accommodation property.

Figure 2:
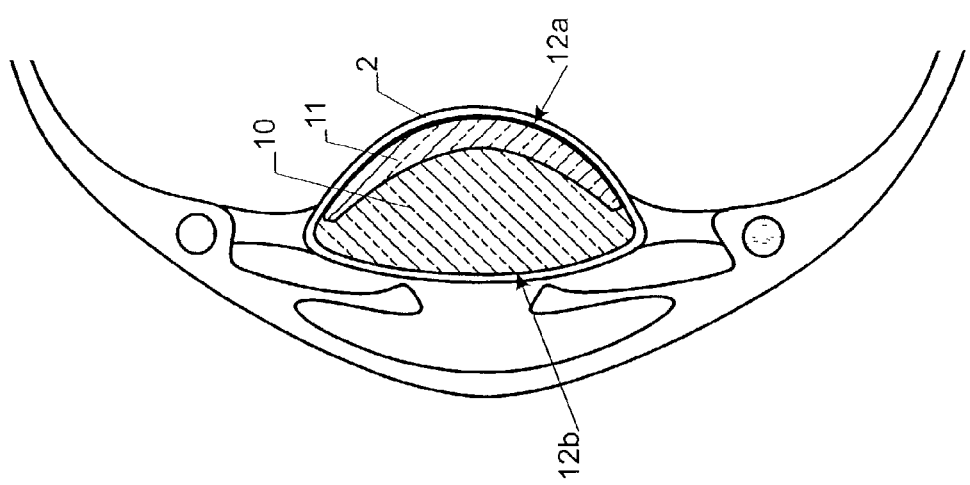
FIG. 2 is a section through an eye with a lens implant.

The present invention relates to a lens implant which replaces the lens body 3 of the eye. Such a lens is illustrated in FIG. 2. It consists of two transparent parts 10, 11 which abut against each other and which together have about the same size and shape as the replaced lens body 3 accommodated to infinity. Thus a distal or convex surface 12a of the lens implant is curved stronger than a proximal surface 12b as is the case at the lens body. The term proximal denotes, in this context, the lens side facing the cornea 5, the term distal the lens side facing the retina (not shown).

The lens implant has the same size and shape as a natural lens body when it has a convex proximal surface with a radius of curvature between 8.4 and 13.8 mm, a convex distal surface with a radius of curvature between 4.6 and 7.5 mm and a thickness between 2.8 and 5.5 mm. The typical equator amounts for eyes of grownups to about 9 to 11 mm. Typical proximal and distal radii of curvature are 10 and 6 mm, respectively.

The lens implant, i.e. specifically its first part 10, features optical and elastic properties which are similar to those of a lens body with a good accommodation capability. It is usually enclosed tightly by the lens capsule 2 and generates, just as a natural lens body, an intracapsulate pressure. Upon contraction of the Müller's muscle 6 the curvature of the surfaces of the lens implant, and accordingly its focal width, changes. Thus, the lens implant gives a natural accommodation capability to the eye. To this end the volume of the first or proximal part 10 should be larger than the one of the second or distal part 11. Preferably also the total diameter perpendicular to the axis should be larger at the first part 10 than at the second part 11.

The two parts 10, 11 of the lens implant preferably feature refractive indices that differ from each other. During the production of the lens the first, proximal part 10 is made to suit the size and shape of the lens body 3 to be replaced whereas the second, distal part 11 is a prefabricated, elastic, shaped body.

When producing the lens the two parts 10, 11 fulfil different objects. The proximal part 10 defines the volume of the lens. The distal part 11 renders stability to the rear lens portion and allows to adjust the focal distance to the respective eye individually. To this end a kit is available for the person skilled in the art for producing the lens which includes the flowable filling material and a plurality of pre-fabricated lens parts. The lens parts differ from each other in their refractive index and/or their shape.

The lens implant is produced by bringing together the flowable filling material and one of the lens parts 10, 11 and the filling material is cured to the desired rigidity. This can proceed outside of the eye or intraoccularly. Hereto, the eye is initially measured in order to determine the focal distance and the shape of the lens body 3 and, respectively, in order to determine from the properties of the eye the desired refractive index of the implant. From this it can be calculated which of the available lens parts 10, 11 shall be used so that the lens implant imitates the desired focal distance as close as possible.

In a preferred production method the lens implant is produced intraoccularly. Hereto, in the first step a small opening is cut into the lens capsule 2 and the lens body 3 is removed. This proceeds preferably by ultrasonics, laser technique, phacoemulsification or laserfakoemulsification. Corresponding methods are known to the person skilled in the art.

The distal part 11 of the lens is introduced thereafter into the lens capsule 2 which has been hollowed accordingly. In order to allow the lens part 11 to be inserted even through such a small opening, it is elastically deformable so that it can be rolled up or folded and be inserted by means of an injection instrument. An instrument of this kind is disclosed e.g. in U.S. Pat. No. 5,620,450.

Figure 3:
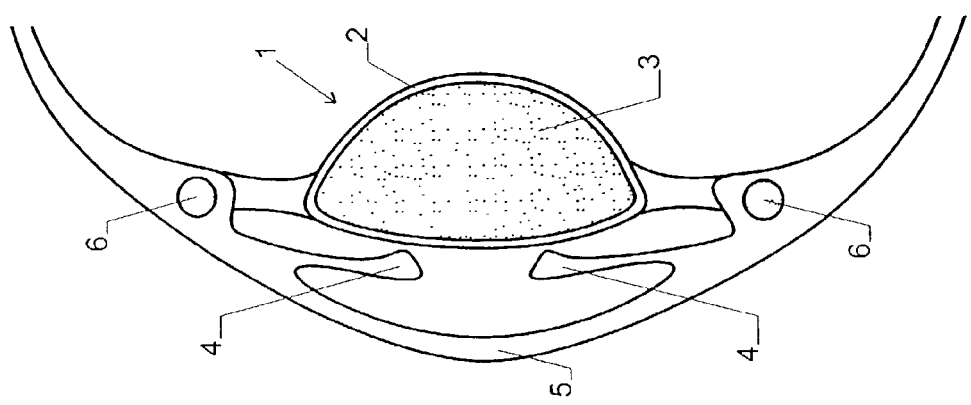
FIG. 3 is a possible production method for the lens implant and
FIG. 4 is a section through an eye with an alternative embodiment of the lens implant.

The distal part 11 which has been inserted extends and roughly attains the desired position in the lens capsule 2. In a relaxed state it has a concave-concave curvature such as is disclosed in FIGS. 2 and 3. It forms the distal side of the lens implant and the shape of its convex surface 12a corresponds to the one of the distal surface of the lens body 3 to be replaced. Depending on what is required from the optical and mechanical properties, the distal part 11 can also be biconvex, i.e. its proximal surface can be bent towards the front or towards the back or be planar.

After the distal lens part 11 has been positioned, the proximal lens part 10 is injected into the lens capsule 2 though an injection apparatus 13 in the form of a filling material in a flowable state and the lens capsule is filled in its state accommodated to infinity. In this step, such an amount of filling material is injected that the volume of the lens implant corresponds substantially to the one of the previously removed lens body.

The lens capsule 2 is, thereafter, closed and the proximal lens part 10 is cured to the desired rigidity, which can be achieved e.g. by a chemically, electrically or optically induced cross-linking. Suitable filling materials and techniques are known to the person skilled in the art e.g. from U.S. Pat. No. 4,608,050 or WO 89/00029.

A cross-linked polysiloxane, a hydrogel or a collagen-preparation can, e.g. be used because regarding it has a consistency similar to the lens body.

Arranging of the pre-fabricated lens part 11 at the distal side of the lens has the advantage that it forms a relatively stable rear wall for the lens. If a clouding occurs after the implanting at the distal area of the lens capsule 2, the lens capsule 2 can be removed in such this area by means of laser rays. The lens part 11 shields also without lens capsule 2 the possibly still flowable, physiologically less compatible first lens part 10 from the vitreous body of the eye and all other structures of the interior of the eye. Because opening of the rear capsule by a laser is never uniform, the softer material of the first lens part would otherwise leak out at the back because the capsule is subjected to pressure. This would destroy the optical function of the lens. Lens part 11 prevents such a leakage.

However, in particular if a more stable, physiologically well compatible material is used for the first lens part 10, the second lens part 11 can e.g. also be located in the center or in a proximal portion of the lens implant.

Figure 4:
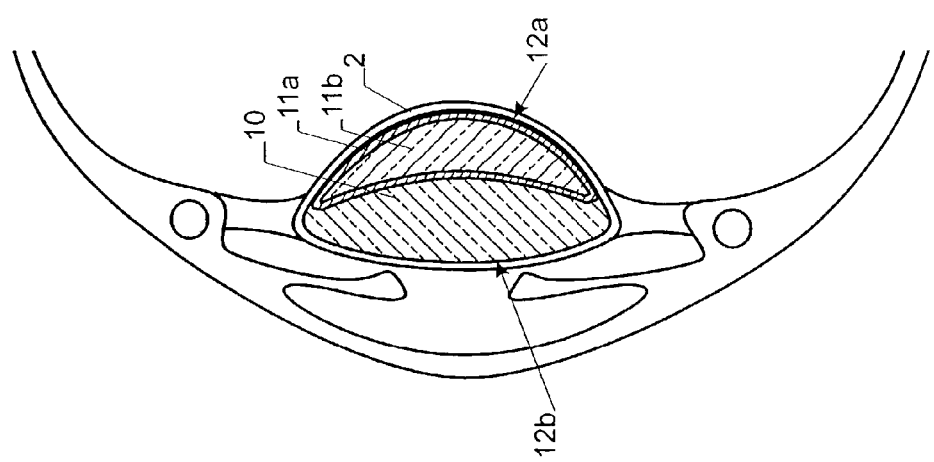

A second embodiment of the invention is illustrated in FIG. 4. Here the distal part 11 consists of a bag 11a which is filled by a transparent filling material 11b. This structure has the advantage of producing a relatively large distal part 11a, 11b without making a large hole in the lens capsule 2. After removing the lens body 3, the bag 11a is first inserted in an empty, rolled state into the lens capsule 2. Thereafter an injection needle is inserted through the same opening. By means of the needle the filling material 11b is fed into the bag 11a. Finally, the proximal part 10 is filled in.

The bag 11a is cut and pre-shaped in such a manner that it attains the desired shape in the filled state. In the kit mentioned above at least a part of the pre-shaped lens parts, in particular the larger ones thereof, may be provided as bags 11a.

Subject of the present invention is a lens implant and a kit for the production of such lens implants. The invention relates, however, also to the above described, intraoccular method of production, in which the filling material for the first part 10 of the lens is introduced in a flowable state and a suitable lens part 11 is introduced in a solid state into the lens capsule 2. Preferably, the rigidity of the first lens part 10 is thereafter increased by a curing. During this, the capsule 2 should be accommodated to infinity.

Whereas in the present application preferred embodiments of the invention are described, it shall be clearly understood that the invention is not limited thereto but can be also embodied otherwise within the scope of the following claims.

What is claimed is:

1. A lens implant for placement into the lens capsule and for replacing the lens body of an eye, the lens implant being shaped like a natural lens body, with a distal surface and a proximal surface, wherein the distal surface has a stronger curvature than the proximal surface, the lens implant comprising:
   a first portion comprising a flowable material which can be cured intra-ocularly to an elastically deformable state;
   and a second portion comprising a solid material having a refractive index or an elastic deformability that differs from the one of the first portion wherein the second portion forms the distal surface, and wherein the first portion forms the proximal surface,
   wherein a diameter of the first portion perpendicular to a focal axis of the lens exceeds a diameter of the second portion.

2. A lens implant for placement into the lens capsule and for replacing the lens body of an eye, the lens implant being shaped like a natural lens body, with a distal surface and a proximal surface, wherein the distal surface has a stronger curvature than the proximal surface, the lens implant comprising:
   a first deformable part, which can be cured from a flowable to an elastically deformable state;
   and a second part having a refractive index or an elastic deformability that differs from the one of the first part, wherein the second part comprises a bag filled by a filling material and forms the distal surface, and wherein the first part forms the proximal surface,
   wherein a diameter of the first part perpendicular to a focal axis of the lens exceeds a diameter of the second part.

3. The lens implant of claim 2, wherein the second part has a refractive index which differs from the one of the first part.

4. The lens implant of claim 2, wherein the first part and the second part abut against each other.

5. The lens implant of claim 2, wherein the second part is elastically deformable for introduction into the lens capsule in a rolled up or folded state.

6. The lens implant of claim 2, wherein the lens implant consists of the first part and the second part.

7. The lens implant of claim 2, wherein a distal side of the second part is curved in its relaxed state for forming the convex distal surface of the lens implant.

8. The lens implant of claim 2 wherein the first part includes at least a material selected from the group consisting of cross-linked polysiloxanes, hydrogels and collagen preparations.

9. The lens implant of claim 2, wherein the first part has a higher deformability than the second part, and in particular that the first part is better elastically deformable than the second part.

10. The lens implant of claim 2, wherein the first part is a gel.

11. The lens implant of claim 2, wherein the proximal surface is convex with a radius of curvature between 8.4 and 13.8 mm, and wherein the distal surface is convex with a radius of curvature between 4.6 and 7.5 mm, and wherein the lens implant has a thickness between 2.8 and 5.5 mm.

12. The lens implant of claim 2, wherein it is dimensioned and shaped in such a manner that it has substantially the dimensions and shape of a natural lens body accommodated to infinity.

13. The lens implant of claim 2, wherein the first part has a volume that exceeds the volume of the second part.

14. A lens implant for placement into the lens capsule and for replacing the lens body of an eye, the lens implant configured to replace a natural lens body, with a distal surface and a proximal surface, wherein the distal surface has a stronger curvature than the proximal surface, the lens implant having a convex proximal surface with a radius of curvature between 8.4 and 13.8 mm, a convex distal surface with a radius of curvature between 4.6 and 7.5 mm, and a thickness between 2.8 and 5.5 mm, said lens implant comprising:
   a first deformable part, which can be cured from a flowable to an elastically deformable state;
   and a second part comprising a bag filled by a filling material and having a refractive index or an elastic deformability that differs from the one of the first part, wherein the second part forms the distal surface, and wherein the first part forms the proximal surface;
   wherein the first part is cureable intraocularly from a flowable to an elastically deformable state.

15. The lens implant of claim 14, wherein the first part has a diameter that exceeds the diameter of the second part.

16. A method of replacing the lens body of an eye by a lens implant, comprising the steps of:
   removing the lens body from the lens capsule of the eye;
   introducing a preshaped, solid, elastically deformable distal lens part into the lens capsule and positioning it at a distal end of the lens capsule; and
   after positioning the distal lens part, introducing a flowable filling material into the lens capsule at a proximal side of the distal lens part for forming of a proximal proximal part of the lens implant, wherein the flowable material is cured intraocularly.

17. The method of claim 16 further comprising the step of:
   selecting the preshaped, solid, elastically deformable lens part out of a set of lens parts with various different refractive indices in accordance to a desired refractive index determined from properties of the eye.

18. The method of claim 16 wherein the flowable filling material is introduced into the lens capsule in an amount such that the lens implant has substantially the same volume as the removed lens body.

19. A method of replacing the lens body of an eye by a lens implant, comprising the steps of:
   removing the lens body from the lens capsule of the eye;
   introducing a preshaped, solid, elastically deformable distal lens part into the lens capsule and positioning it at a distal end of the lens capsule; and
   after positioning the distal lens part, introducing a flowable filling material into the lens capsule at a proximal side of the distal lens part for forming of a proximal proximal part of the lens implant, wherein the eye is accommodated to infinity during a curing of the flowable filling material.

20. A method of replacing the lens body of an eye by a lens implant, the method comprising the steps of:

removing the lens body from the lens capsule of the eye;

introducing a solid, elastically deformable distal lens part into the lens capsule and positioning it at a distal end of the lens capsule;

introducing a flowable filling material into the lens capsule at a proximal side of the distal lens part for forming of a proximal proximal part of the lens implant after the first lens part is positioned; and curing the flowable filling material intraocularly after the flowable filling material has been introduced.

* * * * *